US00PP30990P2

(12) United States Plant Patent
Van Swieten

(10) Patent No.: US PP30,990 P2
(45) Date of Patent: Oct. 29, 2019

(54) ***PHALAENOPSIS* ORCHID PLANT NAMED 'PHALGEPWAL'**

(50) Latin Name: ***Phalaenopsis* hybrid**
Varietal Denomination: PHALGEPWAL

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/998,056

(22) Filed: Jun. 20, 2018

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

(56) References Cited

PUBLICATIONS

UPOV-PLUTO: Plant Variety Database Apr. 11, 2019 citation for 'Phalgepwal' (1 page).*
EU Community Plant Variety Rights Application No. 2017/2375, Application n°A201702688, filed Sep. 26, 2017, 8 pages.
EU Community Plant Variety Office Official Gazette, Jun. 2017, Dec. 15, 2017, cover page and pp. 38, 58.

* cited by examiner

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALGEPWAL', particularly characterized by having small, white flowers with light greenish-yellow lips, 2 to 5 peduncles that are short and sturdy, leaves that are oblong, and is propagated by meristem tissue culture, is disclosed.

3 Drawing Sheets

Genus and species: *Phalaenopsis* hybrid.
Variety denomination: 'PHALGEPWAL'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGEPWAL'.

The new *Phalaenopsis* plant is a product of a planned breeding program conducted by the inventor in Bleiswijk, The Netherlands. The objective of this breeding program was to create a new *Phalaenopsis* plant with numerous attractive, small, white flowers with light greenish-yellow lips, suitable for potted plant production.

The new *Phalaenopsis* plant 'PHALGEPWAL' is a result of cross-pollination made by the inventor in April 2009 in Bleiswijk, The Netherlands of the proprietary female, or seed parent, *Phalaenopsis* hybrid '11968-04' (unpatented) with the proprietary male, or pollen parent, *Phalaenopsis* hybrid '01-3275' (unpatented).

The new *Phalaenopsis* was selected by the inventor as a single plant within the progeny of the stated cross-pollination in a controlled greenhouse in Bleiswijk, The Netherlands in March 2012. Asexual reproduction of the new *Phalaenopsis* plant by meristem tissue culture since 2014 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 26, 2017. 'PHALGEPWAL' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALGEPWAL' as a new and distinct variety of *Phalaenopsis* plant.

1) Small, white flowers with light greenish-yellow lips;
2) 2 to 5 peduncles;
3) Peduncle is short and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in May 2018. Colors in the photographs may differ from the color values cited in the detailed botanical description, which accurately describe the actual colors of the new variety.

DESCRIPTION OF THE NEW VARIETY

Figure 1:
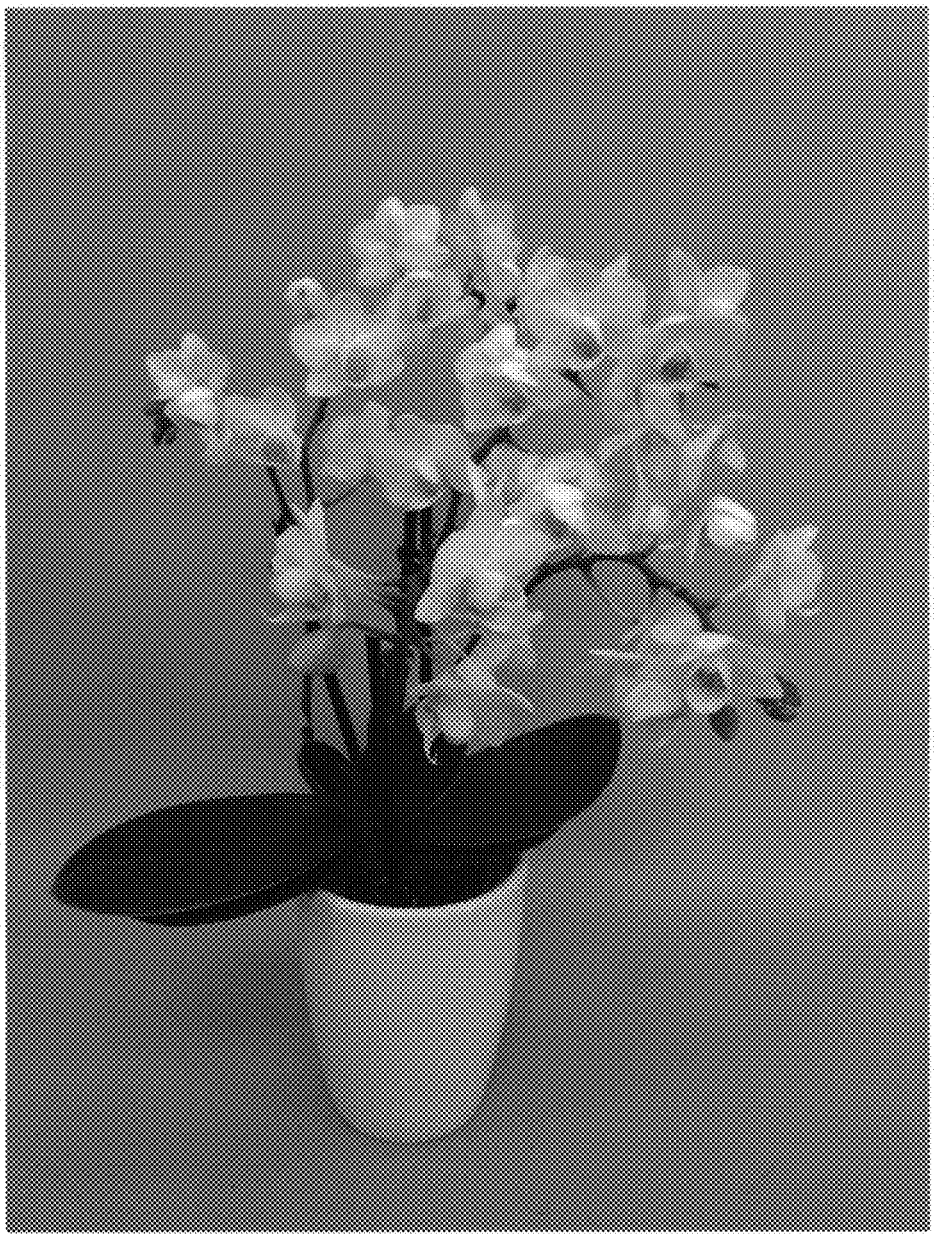
FIG. 1 shows the overall plant habit, including blooms, buds and foliage of 'PHALGEPWAL'.
Figure 2:
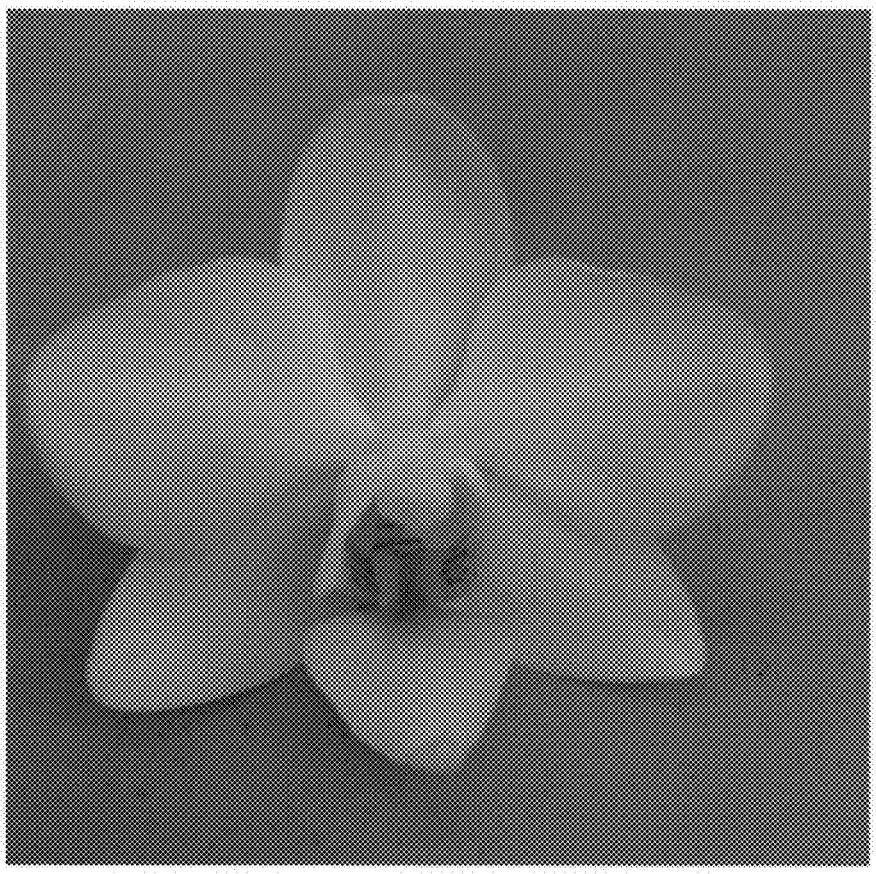
FIG. 2 shows a close-up of a flower of 'PHALGEPWAL'.
Figure 3:
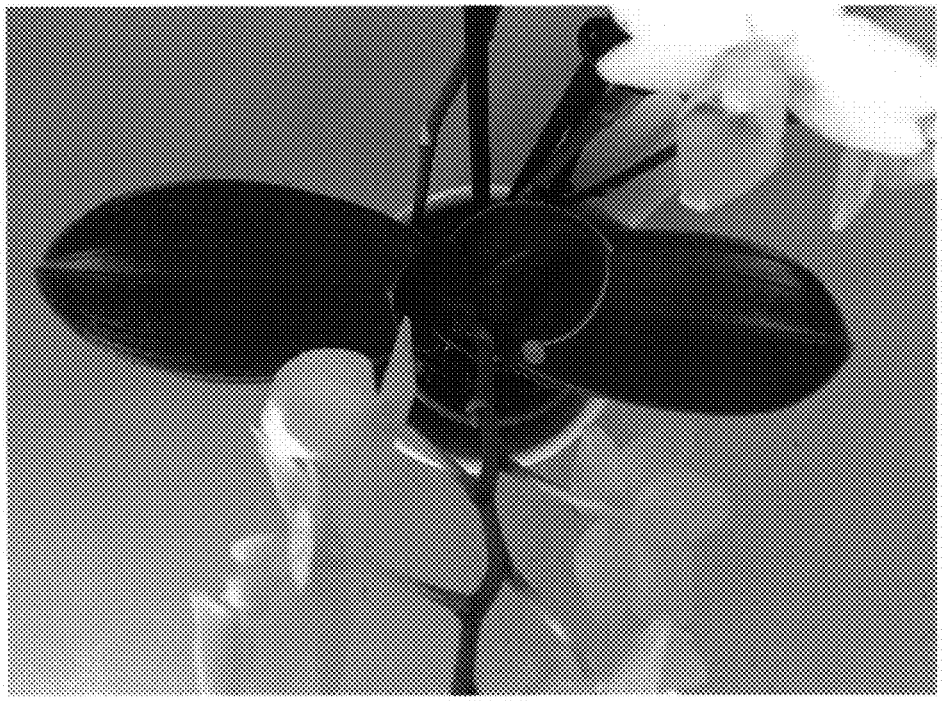
FIG. 3 shows an overhead view of the leaves and flowers of 'PHALGEPWAL'.

The following detailed description sets forth the distinctive characteristics of 'PHALGEPWAL'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in May 2018 on flowering plants which were planted in 6 centimeter (diameter) pots. After in-vitro propagation, the plants were directly transplanted into 6 centimeter (diameter) pots and grown in a greenhouse between 27° C. to 29° C. for 32 weeks, continued by a cooling period of 6 weeks between 18° C. to 20° C. and 12 weeks in a greenhouse of 21° C. Flowering occurs after 50-weeks in a 6 centimeter pot.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGEPWAL'.

Parentage:

*Female parent*.—*Phalaenopsis* cultivar '11968-04' (unpatented).

*Male parent*.—*Phalaenopsis* cultivar '01-3275' (unpatented).

Propagation:

*Type*.—Meristem tissue culture.

Roots:

*Root description*.—Greyed-green colored roots (between RHS 190B and 190C) with branching lateral roots having yellow-green (RHS 146D) colored root tips.

Plant:

*Commercial crop time to flowering*.—Following asexual propagation (in-vitro), the plants are directly transplanted into 6 cm pots. The plants are finished after 48 to 50 weeks.

*Growth habit of peduncle*.—Standard, green leaves, raceme to panicle.

*Height (from soil level to top of inflorescence)*.—Approximately 22.0 cm to 27.0 cm.

*Width (measured from leaf tips)*.—About 18.0 cm to 20.0 cm.

*Vigor*.—Moderate.

Leaves:

*Mature leaves*.—Quantity per plant: 7 to 10 leaves are produced before flowering. Length (fully expanded): 8.5 cm to 9.5 cm. Width: 4.0 cm to 5.0 cm. Shape: Oblong. Base shape: Moderately elongated. Apex: Obtuse unequal. Leaf blade angle with the petiole (measured from the horizontal position): Between 10 degrees and 25 degrees. Leaf margin: Entire. Color: Upper surface: RHS 147A with light yellow-green edge (RHS N144A). Lower surface: RHS 147B with small light yellow-green edge (RHS N144A). Texture: Smooth. Thickness: 1.6 mm to 1.9 mm. Venation: Pattern: Parallel. Color of the midvein: Upper surface: RHS 147A. Lower surface: RHS 147B.

Peduncle:

*Quantity per plant*.—2 to 5.

*Number of flowers per peduncle*.—13 to 23.

*Length*.—22.0 cm to 27.0 cm.

*Diameter*.—2.8 mm to 3.3 mm.

*Strength*.—Moderate.

*Aspect*.—Upright to slightly pendant.

*Texture*.—Smooth.

*Color*.—Green (RHS 146A).

*Internode length*.—1.5 cm to 2.5 cm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 110.0 mm to 160.0 mm.

*Flowering time*.—First flowers can be expected 10 to 11 months after planting in a 6 cm (diameter) pot.

*Flower*.—Height: 27.0 mm to 32.0 mm. Diameter: 35.0 mm to 40.0 mm. Depth of lip: 11.0 mm to 13.0 mm.

*Flower longevity*.—On the plant: 8 to 12 weeks.

*Fragrance*.—Absent.

*Flower bud*.—Average size: Small to medium. Length: 11.0 mm to 13.0 mm. Width: 9.0 mm to 11.0 mm. Shape: Egg shaped. Color: Yellow-green (RHS 150C) at the base and light yellow-green toward the top (mix between RHS 150D and 145D).

*Petals*.—Arrangement: Open/free. Shape: Semi-circular. Apex: Rounded asymmetric. Margin: Slightly undulated. Length (from base to tip): 15.0 mm to 17.0 mm. Width: 15.0 mm to 17.0 mm. Color (when fully opened): Upper surface: Basic color: White (RHS NN155C). Over color: Absent. Lower surface: Basic color: White (RHS NN155C). Over color: Absent.

*Dorsal sepal*.—Shape: Elliptic. Apex: Rounded to slightly emarginated. Margin: Entire. Length (from base to tip): 16.0 mm to 18.0 mm. Width: 11.0 mm to 13.0 mm. Color (when fully opened): Upper surface: Basic color: White (RHS NN155C). Over color: Absent. Lower surface: Basic color: White (RHS NN155C). Over color: Slightly light purple (RHS 76C) at the base.

*Lateral sepals*.—Shape: Ovate. Apex: Obtuse asymmetric. Margin: Entire. Length (from base to tip): 19.0 mm to 21.0 mm. Width: 12.0 mm to 14.0 mm. Color (when fully opened): Upper surface: Basic color: White (RHS NN155C). Over color: Absent. Lower surface: Basic color: White (RHS NN155C). Over color: Slightly light purple base and vein toward the tip (RHS 76C); light green (RHS 145C).

*Labellum (lip)*.—Whiskers: Present. Length of whiskers: 3.0 mm to 5.0 mm. Color of whiskers: White (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 12.0 mm to 14.0 mm. Width: 7.0 mm to 9.0 mm. Color: Upper surface: White (RHS NN155C) with purple-red stripes (RHS 61A) at the base and yellow margin (RHS 7A) on one side. Lower surface: White (RHS NN155C) with a small yellow margin (RHS 6A) on the front side.

*Apical lobe*.—Shape: Triangular/ovate. Margin: Entire. Length: 13.0 mm to 15.0 mm. Width: 12.0 mm to 14.0 mm. Color: Upper surface: Yellow (RHS 7A) at the base and white (RHS NN155C) toward the whiskers. Lower surface: White (RHS NN155C) with a small yellow margin (RHS 6A) on the front side.

*Callus*.—Average size: Small. Height: 4.0 mm to 5.0 mm. Length: 4.0 mm to 5.0 mm. Width: 3.0 mm to 4.0 mm. Color: Yellow (between 8A and 8B) dotted (RHS 61A).

Reproductive organs:

*Column*.—Length: 7.0 mm to 9.0 mm. Diameter: 3.1 mm to 3.4 mm. Color: White (RHS NN155C).

*Pollinia*.—Quantity: 2. Diameter: 0.7 mm to 0.9 mm. Color: Orange (RHS 24A).

*Ovary*.—Length: 6.0 mm to 8.0 mm. Diameter: 1.0 mm to 1.3 mm.

*Pedicel*.—Length: 19.0 mm to 21.0 mm. Diameter: 1.3 mm to 1.6 mm. Color: Light yellow-green (RHS 145C) and purple-red at the base (RHS N77D); light yellow-green toward the flower (RHS 145D) and (RHS 157D).

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGEPWAL' differs from female parent plant '11968-04' (unpatented) in that 'PHALGEPWAL' has apical lobes with yellow at the base and white toward the whiskers, and lateral sepal upper surfaces with no over color, whereas '11968-04' has apical lobes that are yellow-green and white toward the whiskers, and lateral sepal upper surfaces with over color. Additionally, 'PHALGEPWAL' has smaller flowers than '11968-04'.

The male parent plant of 'PHALGEPWAL', cultivar '01-3275', is no longer in existence, so a meaningful comparison cannot be made.

'PHALGEPWAL' is most similar to the commercial *Phalaenopsis* plants named 'PHALDUXI' (U.S. Plant Pat. No. 25,680) and 'PHALDUXHA' (U.S. Plant Pat. No. 28,943). 'PHALGEPWAL' differs from the commercial variety 'PHALDUXI' in that 'PHALGEPWAL' has a rounded asymmetric petal apex, whereas 'PHALDUXI' has a mucronate symmetric petal apex. Additionally, 'PHALGEPWAL' has shorter whiskers and smaller flowers than 'PHALDUXI'.

'PHALGEPWAL' differs from the commercial variety 'PHALDUXHA' in that 'PHALGEPWAL' has a rounded asymmetric petal apex, whereas 'PHALDUXHA' has an obtuse asymmetric petal apex. Additionally, 'PHALGEPWAL' has shorter whiskers and smaller flowers than 'PHALDUXHA'.

I claim:

1. A new and distinct variety of *Phalaenopsis* plant named 'PHALGEPWAL', substantially as described and illustrated herein.

* * * * *